(12) United States Patent
Catoe

(10) Patent No.: US 9,138,358 B2
(45) Date of Patent: Sep. 22, 2015

(54) CLOTH DIAPER

(76) Inventor: Jenny K. Catoe, Elgin, SC (US)

( * ) Notice: Subject to any disclaimer, the term of this patent is extended or adjusted under 35 U.S.C. 154(b) by 854 days.

(21) Appl. No.: 13/218,497

(22) Filed: Aug. 26, 2011

(65) Prior Publication Data

US 2013/0053805 A1 Feb. 28, 2013

(51) Int. Cl.
| A61F 13/15 | (2006.01) |
| A61F 13/20 | (2006.01) |
| A61F 13/49 | (2006.01) |
| A61F 13/493 | (2006.01) |
| A61F 13/56 | (2006.01) |

(52) U.S. Cl.
CPC ..... *A61F 13/49003* (2013.01); *A61F 13/15268* (2013.01); *A61F 13/493* (2013.01); *A61F 13/5638* (2013.01); *A61F 2013/15276* (2013.01)

(58) Field of Classification Search
USPC ............. 604/385.01, 385.03, 385.11, 385.14, 604/385.15, 385.22, 386–387, 393, 604/397–400
See application file for complete search history.

(56) References Cited

U.S. PATENT DOCUMENTS

| 5,190,533 A | 3/1993 | Blackburn |
| 5,350,370 A | 9/1994 | Jackson et al. |
| 5,407,438 A | 4/1995 | Hedlund et al. |
| 5,820,973 A | 10/1998 | Dodge, II et al. |
| 5,843,852 A | 12/1998 | Dutkiewicz et al. |
| 6,579,273 B2 | 6/2003 | Dupuny |
| 7,629,501 B2 | 12/2009 | Labit et al. |
| 2005/0065487 A1 | 3/2005 | Graef et al. |
| 2005/0256490 A1 | 11/2005 | Genke |
| 2008/0195075 A1 | 8/2008 | Ruocco |
| 2010/0168709 A1* | 7/2010 | Hodgkin .................. 604/385.14 |
| 2010/0179495 A1* | 7/2010 | Roe .............................. 604/367 |
| 2010/0204668 A1 | 8/2010 | Yang |

* cited by examiner

*Primary Examiner* — Michele M Kidwell
(74) *Attorney, Agent, or Firm* — Thomas L. Moses; Southeast IP Group, LLC

(57) ABSTRACT

A reusable, cloth diaper of singular construction is provided. The diaper is generally shaped like a classic hourglass configuration, and includes a pair of absorbent flaps in a cross-flap configuration on an inner portion thereof, wherein one flap is attached to a rear portion of the diaper and the other flap is attached to a front portion of the diaper, each adjacent to the child's waist. The outer layer of the diaper is preferably made from a blend of bamboo and cotton, and includes a polyurethane laminate layer on the inner surface of the outer layer. The diaper construction further includes means for adjusting waist and crotch sizes, as well as storage snap means for securing the diaper into a rolled up storage and transport configuration.

6 Claims, 7 Drawing Sheets

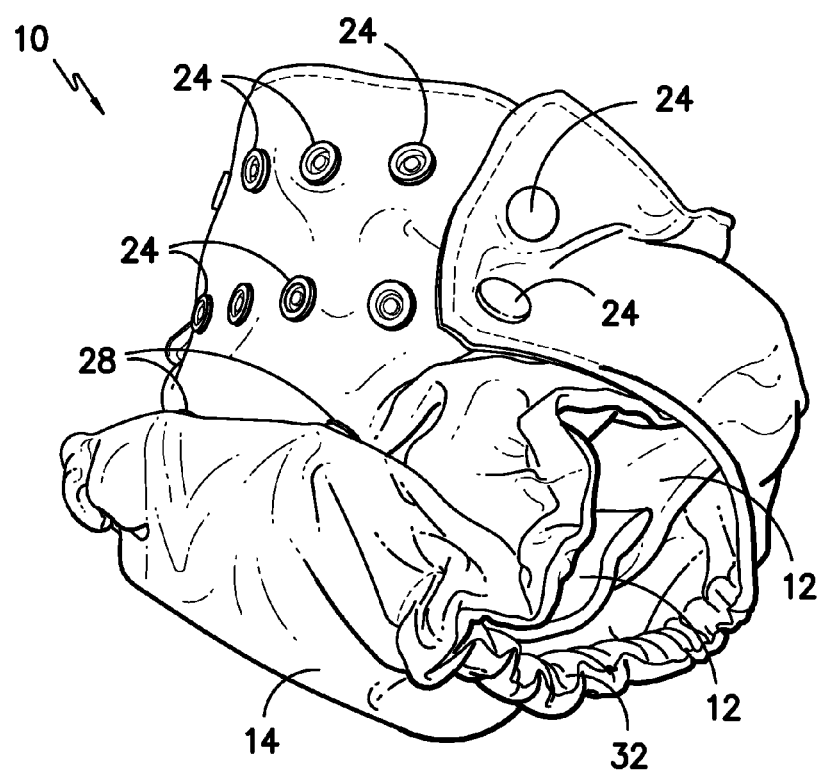
FIG. -1-

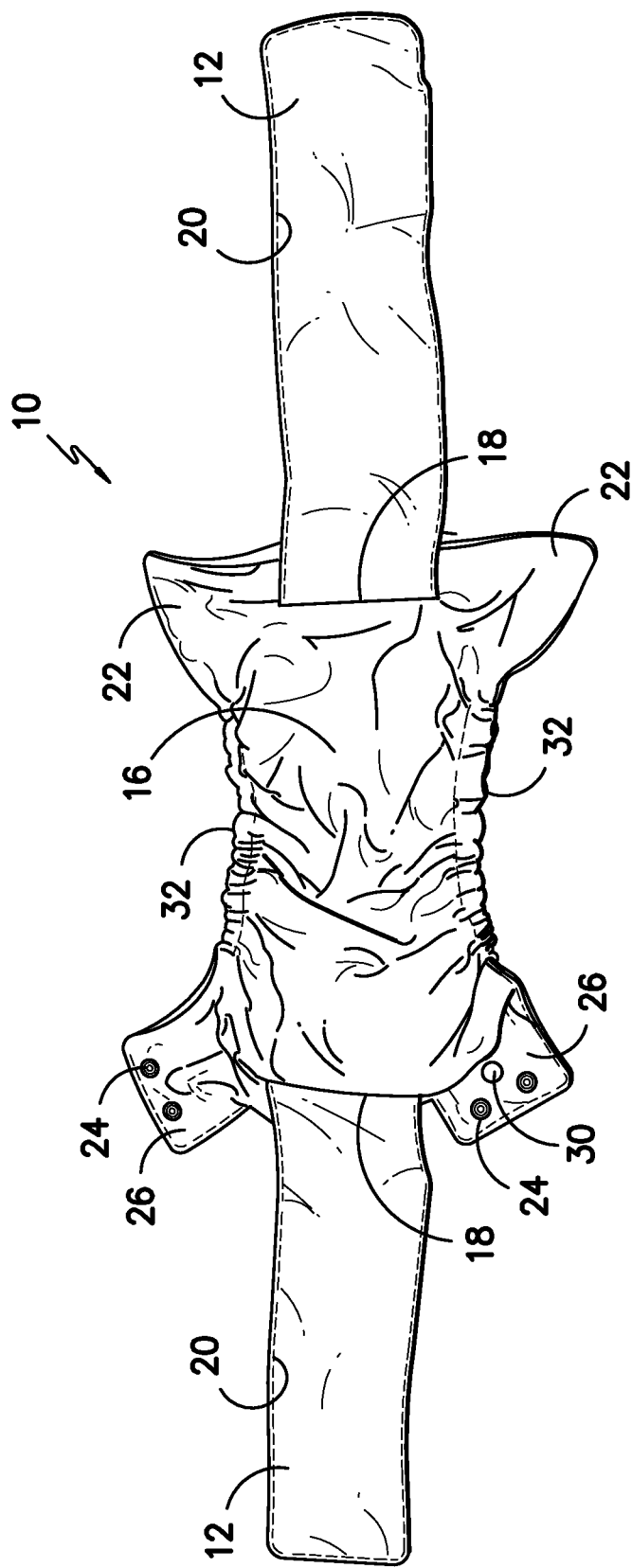
FIG. -2-

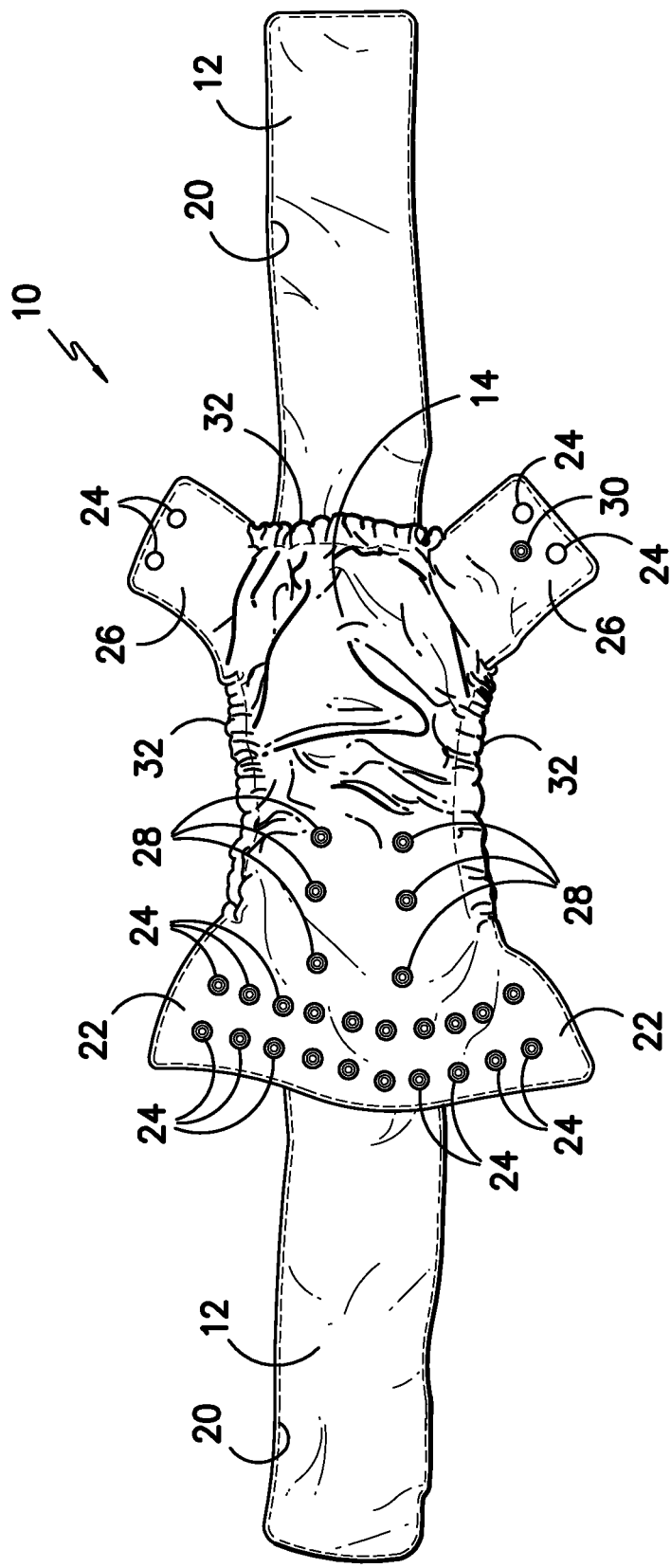
FIG. -3-

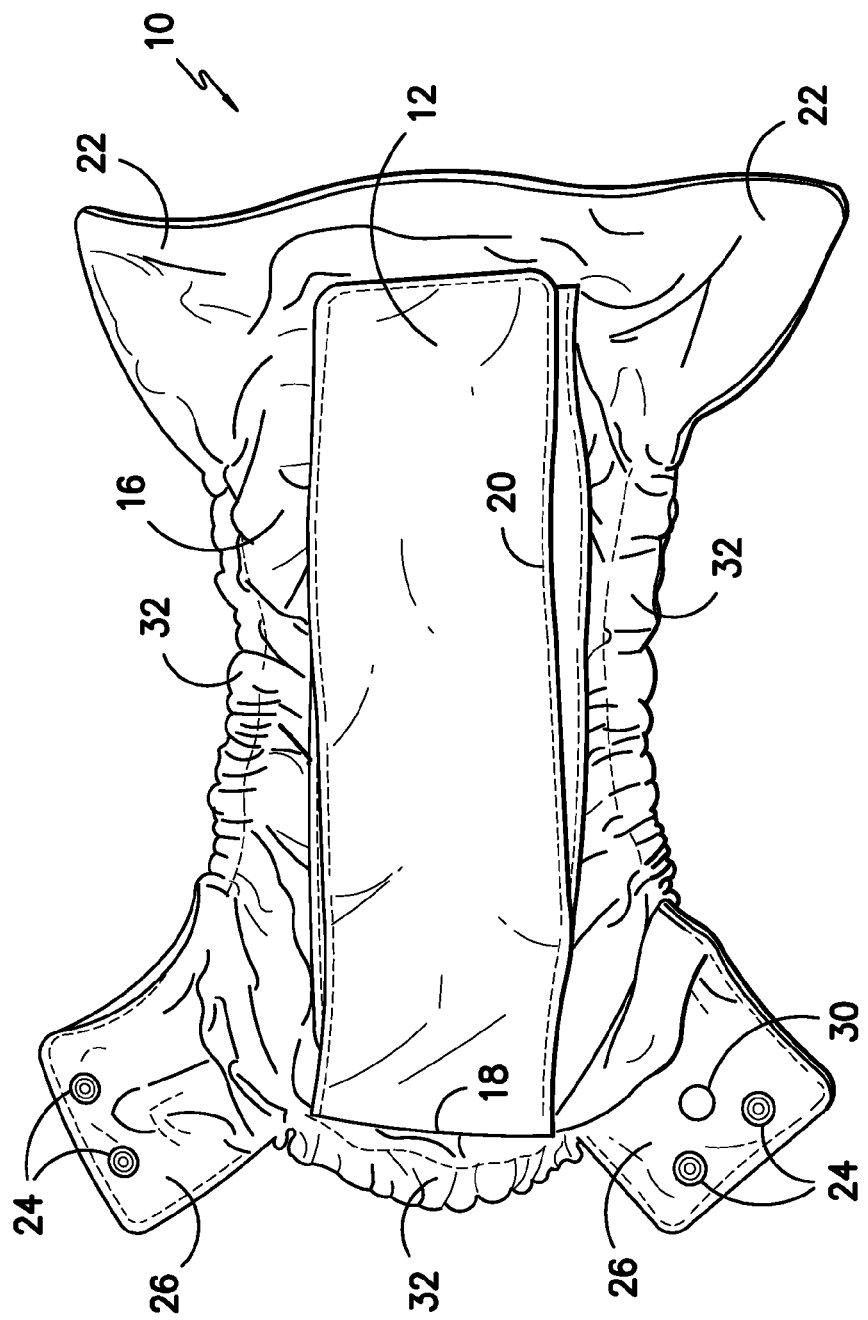
FIG. -4-

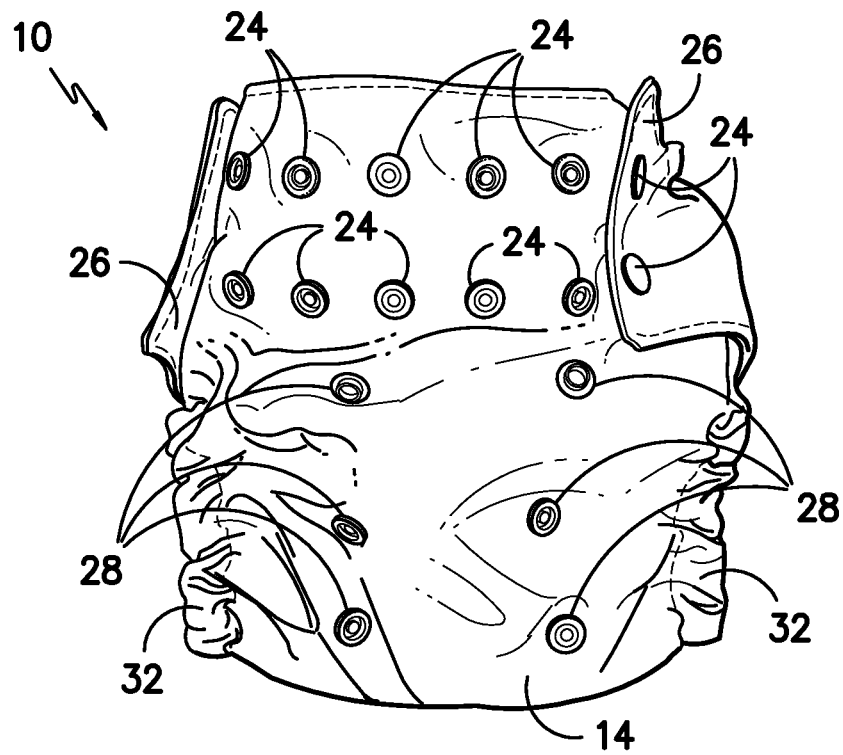
FIG. -5-
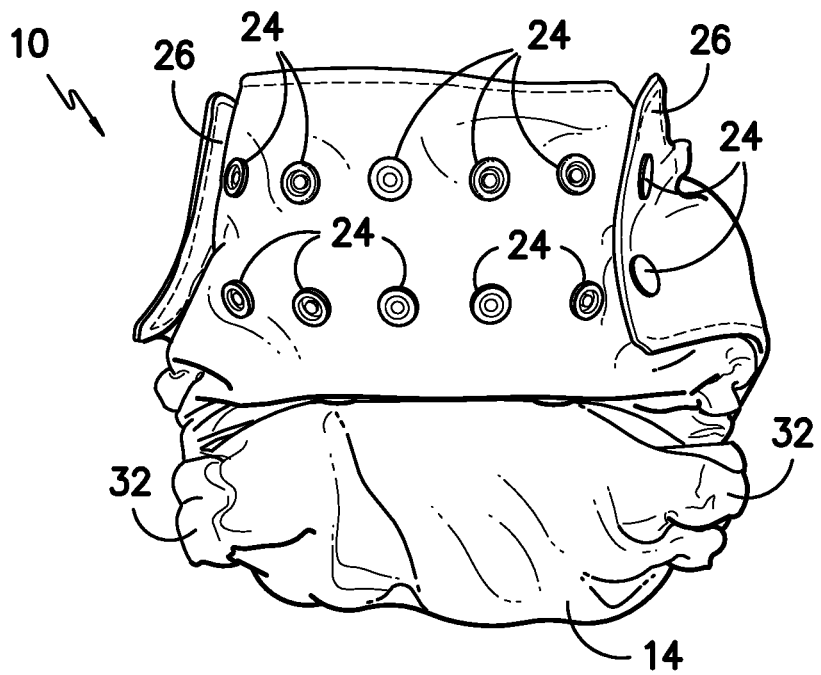
FIG. -6-

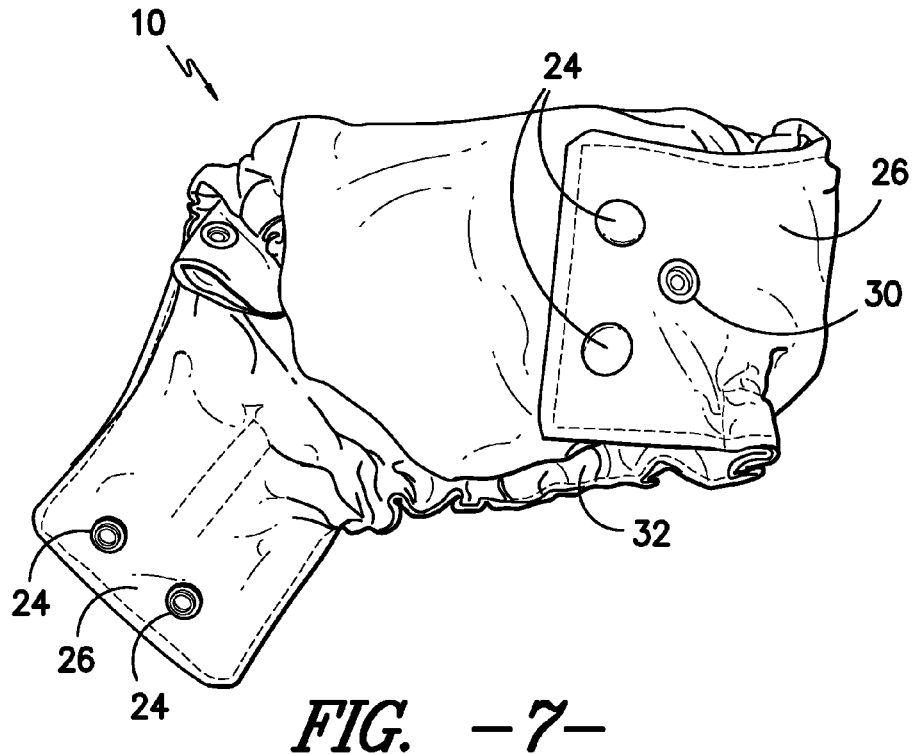
FIG. -7-
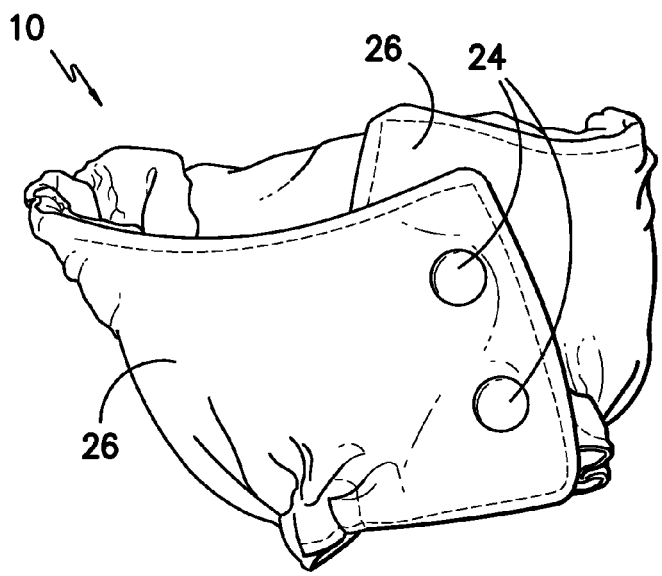
FIG. -8-

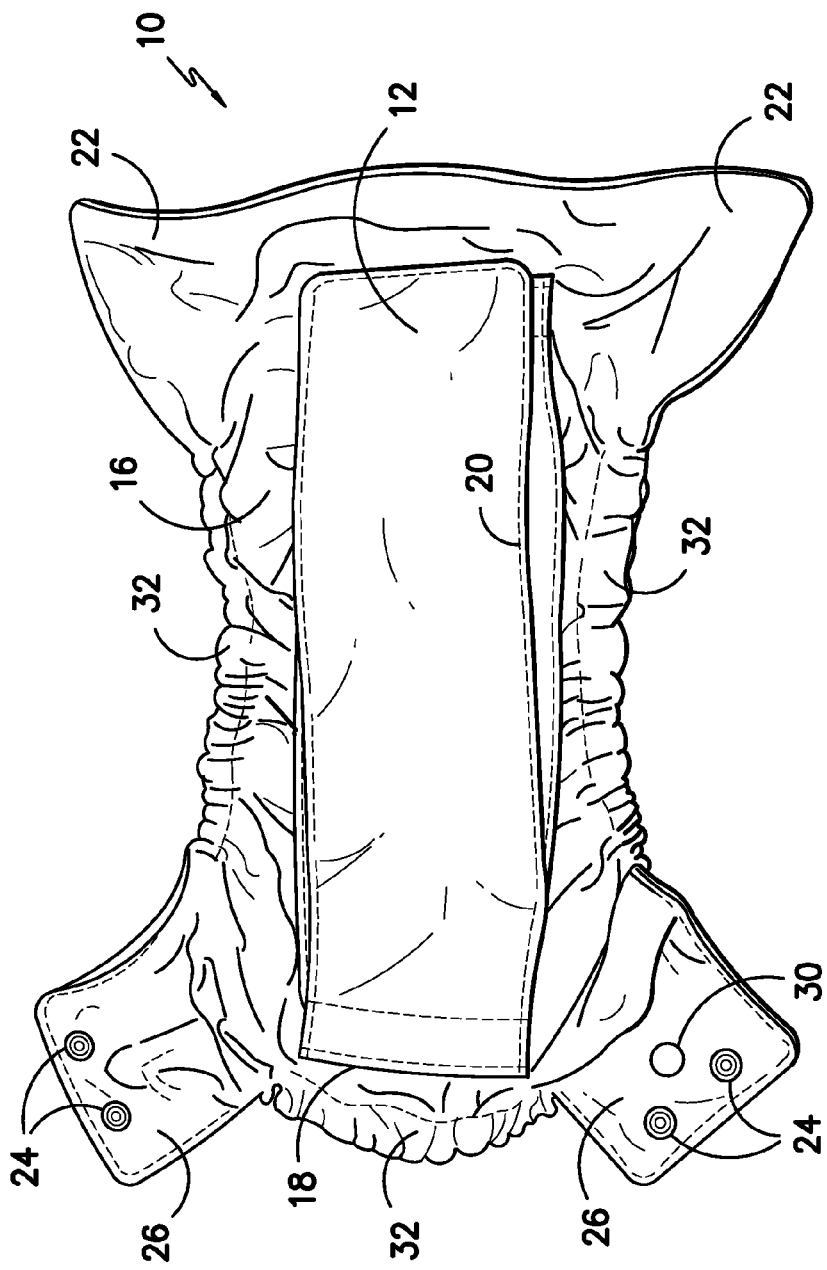
FIG. -9-

CLOTH DIAPER

BACKGROUND OF THE INVENTION

The present invention relates generally to reusable, cloth diapers. More specifically, the present invention relates to a novel diaper assembly that incorporates a moisture resistant outer layer made partially from bamboo and a polyurethane laminate, as well as a construction that allows the diaper to dry more efficiently after washing.

Currently, there are a variety of different diapers on the market, including conventional cloth diapers that are washable and reusable, cloth diapers that include washable or disposable inserts, and disposable diapers. Each type of diaper has its own advantages and disadvantages. Disposable diapers are relatively easy to use, but can be expensive to purchase and create significant amounts of waste that requires disposal, often in landfills. Cloth diapers with disposable inserts may be washed and reused, but the disposable inserts must be replaced and old ones disposed of, and thus include many of the same issues as disposable diapers. Other types of cloth diapers may include reusable inserts, but washing and keeping track of the diapers and reusable inserts involves additional effort and steps. Additionally, cloth diapers today are typically made out of cotton, polyester, or a blend thereof, which causes them to become saturated quickly, thus requiring the use of an additional outer waterproof cover that incorporates a urethane inner liner. There are also diapers that are called "all-in-one" diapers, which combines the diaper with a protective waterproof outer cover that is traditionally made from cotton or polyester with a polyurethane laminate. This polyurethane laminate is generally disposed on the outer portion of the diaper, which makes the outside of the diaper scratchy with a plastic feel to it.

Thus, it would be desirable to provide a diaper having a singular construction including includes a moisture resistant outer layer that has a soft, cloth-like feel to it, and wherein the construction allows the diaper to dry more quickly and efficiently, thus saving time and energy costs associated with the washing/drying process.

BRIEF SUMMARY OF THE INVENTION

In accordance with one aspect of the invention, a reusable, cloth diaper of singular construction is provided. The diaper is generally shaped like a classic hourglass configuration, and includes a pair of absorbent flaps on an inner portion thereof, wherein one flap is attached to a rear portion of the diaper and the other flap is attached to a front portion of the diaper, each adjacent to the child's waist. The outer layer of the diaper is preferably made from a blend of bamboo and cotton, and includes a polyurethane laminate layer on the inner surface of the outer layer.

The front of the diaper includes a pair of front wings and two horizontal rows of snaps with the operative side of the snaps facing outwardly, and the rear of the diaper includes a pair of rear wings, including a pair of snaps, wherein the operative side of the snaps faces inwardly, and these rear snaps correspond to the snaps on the front wings. These front and rear snaps may be operatively connected together to affix the rear of the diaper to the front of the diaper when the diaper is positioned on a child, forming holes for the legs on either side. The rear snaps may be attached to any pair of the front snaps, which allows the waistline of the diaper to be adjusted according to the size of the child.

In use, the absorbent flaps overlap one another on the inside of the diaper, and in a preferred embodiment, each absorbent flap is made from three layers of jersey fleece material, with the fleece side facing inwardly within the flap. The cross-flap configuration allows the layers of material to be spread out during the drying process, which allows the diaper to dry more quickly and efficiently, thus reducing time and energy usage during the drying process.

Two vertical rows of snaps are positioned on the front of the diaper beneath the two horizontal rows of snaps. In a preferred embodiment, there are three snaps in each vertical row, and the top pair of vertical snaps may be operatively connected either to the middle pair or the bottom pair of snaps, in order to adjust the size of the diaper and prevent the diaper from being too large or saggy on the child.

Additionally, one of the rear wings includes an additional storage snap facing outwardly. This arrangement allows the diaper to be rolled up into a ball, and the storage snap may be operatively connected to either of the snaps on the opposed rear wing in order to maintain the diaper in a tight ball for storage or transport.

BRIEF DESCRIPTION OF THE DRAWINGS

These and other features, aspects, and advantages of the present invention will become better understood with regard to the following description, appended claims, and accompanying drawings where:

FIG. 1 is a perspective view of one embodiment of a cloth diaper shown as if in use on a child with vertical adjustment snaps operatively connected to reduce the size and volume of the diaper;

FIG. 2 is a top view of one embodiment of a cloth diaper, showing the inside of the diaper and the snaps on the rear wings thereof, and further showing the opposed absorbent flaps, one flap extending from a front side of the diaper and the other flap extending from a rear portion of the diaper;

FIG. 3 is a top view of one embodiment of a cloth diaper, showing the outside of the diaper having snaps for attachment of the diaper to a child, as well as additional snaps for size adjustment thereof, and further showing the opposed absorbent flaps, one flap extending from a front side of the diaper and the other flap extending from a rear portion of the diaper;

FIG. 4 is a top view of one embodiment of a cloth diaper, wherein the opposed absorbent flaps are shown in overlaying position, with one flap overlaying the other;

FIG. 5 is a front view of one embodiment of a cloth diaper, wherein the rear wings of the diaper are snapped to the front wings of the diaper in operative position for use on a child;

FIG. 6 is a front view of the cloth diaper shown in FIG. 5, wherein the vertical adjustment snaps are engaged with one another to reduce the size and volume of the diaper;

FIG. 7 is a front view of one embodiment of a cloth diaper in a rolled up storage position with the storage snap and one rear wing disengaged from the other;

FIG. 8 is a front view of one embodiment of a cloth diaper in a rolled up storage position, with the rear flaps engaged with one another using the storage snap; and FIG. 9 is a top view of one embodiment of a cloth diaper, wherein the opposed absorbent flaps are shown in overlaying position, with one flap overlaying the other, and further showing an additional seam across the top flap for securing an inner layer of absorbent material in position between the outer layers of the absorbent flap.

DETAILED DESCRIPTION OF THE INVENTION

The present invention includes, in a first embodiment, a reusable, washable cloth diaper 10 having a generally hourglass configuration, and including a pair of absorbent flaps 12, wherein one flap 12 is attached to a front portion of the diaper 10 and the other flap 12 is attached to a rear portion, as shown in FIGS. 2 and 3. The outer layer 14 of the diaper includes a moisture resistant barrier on an inner surface, and the outer layer 14 is preferably made from a blend of bamboo and cotton. The use of bamboo as a component in the outer layer 14 provides certain advantages over other materials. For instance, bamboo does not retain odors to the same degree as other materials, and tends to be more absorbent than cotton, polyester, hemp and the like. In a preferred embodiment, the moisture resistant barrier is a polyurethane laminate. The inside layer 16 of the diaper is preferably made from bamboo jersey fleece material, with the jersey side on the outer surface of the inner layer 16 (in contact with a child's skin), and the fleece portion on the inside surface thereof for purposes of absorbency and wicking moisture away from the child's skin.

Each of the absorbent flaps 12 preferably includes three layers of bamboo jersey fleece fabric. The fleece side of the fabric is disposed on the inside of the flap, while the jersey portion faces outwardly, which helps to wick any moisture away from the child's skin and toward the inside of the flaps. Each flap 12 is sewn onto the diaper, one flap 12 on a front portion of the diaper, and one flap 12 on the rear portion of the diaper, so that the flaps 12 may overlay one another when the diaper is in use, as shown in FIGS. 1, 4, and 9. The flaps 12 are constructed so that the seam 18 connecting the flap 12 to the diaper 10 only penetrates the outer two layers of fabric, and does not include the inner layer of fabric within the flap 12. This arrangement helps to facilitate drying, because a seam 18 including only two layers of compressed fabric, particularly adjacent the diaper 10 itself, will dry more quickly than a seam penetrating three layers. Optionally, a second seam adjacent to and parallel with the seam attaching the flap to the diaper may be used in order to secure the inner layer in position within the two outer layers (as shown in FIG. 9), which prevents the inner layer from bunching up on the inside portion of the flap 12. A serger stitch 20 is preferably used around the perimeter of each flap 12, and penetrates all three fabric layers. Because the serger stitch 20 is only used around the periphery of the flaps 12, which may move freely in a dryer, the flaps 12 may dry more quickly and efficiently. Additionally, because the flaps 12 are attached on opposed sides of the diaper 10, and may move freely with respect to one another and be spread out, the amount of time and energy necessary for drying the diaper 10 after washing is reduced significantly.

The front of the diaper 10 includes a pair of front wings 22 and two horizontal rows of snaps 24 with the operative side of the snaps 24 facing outwardly, and the rear of the diaper includes a pair of rear wings 26, each including a pair of snaps 24, wherein the operative sides of the snaps 24 face inwardly, and these rear snaps 24 correspond to the snaps 24 on the front wings 22. These front and rear snaps 24 may be operatively connected together to affix the rear wings 26 of the diaper 10 to the front wings 22 of the diaper 10 when the diaper 10 is positioned on a child, forming holes for the legs on either side, as shown in FIGS. 1, 5 and 6. The rear snaps 24 may be attached to any pair of the front snaps 24, which allows the waistline of the diaper 10 to be adjusted according to the size of the child.

Two vertical rows of snaps 28 are positioned on the front of the diaper 10 beneath the two horizontal rows of snaps 24. In a preferred embodiment, there are three snaps 28 in each vertical row, and the top pair of vertical snaps 28 may be operatively connected either to the middle pair or the bottom pair of snaps 28, in order to adjust the size of the diaper 10 and prevent the diaper 10 from being too large or saggy on the child, as shown in FIGS. 1 and 6.

Additionally, one of the rear wings 26 includes an additional storage snap 30 facing outwardly. This arrangement allows the diaper 10 to be rolled up into a ball, and the storage snap 30 may be operatively connected to either of the snaps 24 on the opposed rear wing 26 in order to maintain the diaper 10 in a tight ball for storage or transport, as shown in FIGS. 7 and 8.

Along the narrow portion of the hourglass shape of the diaper, elastic material 32 is disposed within the material that forms the leg holes, and is attached to the bottom portion of the front wing 22 and the rear wing 26. The elastic material 32 is not attached to the surrounding material along the course of the sides, so that the material may freely move back and forth along the elastic material 32. Similarly, elastic material 32 is disposed along the rear edge of the diaper between the rear wings, so that the elastic material 32 is not connected to the surrounding material, but is only connected at the ends thereof, adjacent the rear wings 26. This arrangement allows the material to settle into a comfortable position around the legs and back of the child, without bunching up in any one place or position.

The bamboo cotton blend, which is the preferred material for the outer layer of material on the diaper, is preferably 70% bamboo and 30% organic cotton, and includes a polyurethane laminate on an inside surface thereof. Having the polyurethane moisture barrier on the inside surface of the outer layer 14 prevents moisture from leaking through the outside of the diaper 10, and further allows the outside of the diaper 10 to have a fabric feel to it, as opposed to the crinkly plastic feel that is normally associated with the moisture barrier of other diapers.

The present diaper construction, in a preferred embodiment, allows for multiple size adjustments (waist and crotch), includes a moisture barrier in combination with a bamboo cotton blend that feels like cloth, and includes enclosed elastic sides (legs and back) that prevent bunching up and discomfort typically caused by elastic sections of traditional diapers. The cross-flap configuration increases the surface area of the diaper material during washing and drying, in order to achieve more thorough cleaning, as well as less time and energy consuming drying processes. The storage snap assembly allows the diaper to be rolled up into a small ball and secured in that position for transport and storage in such a way that the soiled portion of the diaper is not outwardly exposed.

Although the present invention has been described in considerable detail with reference to certain preferred versions thereof, other versions are possible. Therefore, the spirit and scope of the appended claims should not be limited to the description of the preferred versions contained herein. All features disclosed in this specification may be replaced by alternative features serving the same, equivalent or similar purpose, unless expressly stated otherwise. Thus, unless expressly stated otherwise, each feature disclosed is one example only of a generic series of equivalent or similar features.

What is claimed is:
1. A reusable, washable cloth diaper comprising:
an inner layer of material and an outer layer of material formed into a generally hourglass configuration, wherein said outer layer includes a bamboo component, and further includes a moisture resistant barrier on an inner surface thereof;

said diaper including a pair of rear wings and a pair of front wings, said front and rear wings including attachment means for securing said rear wings to said corresponding front wings;

a first flap of absorbent material attached to a front portion of said diaper;

a second flap of absorbent material attached to a rear portion of said diaper;

wherein said first flap and said second flap may be positioned in overlapping relation when said diaper is in use on a child;

means for adjusting the waist size of said diaper; and means for adjusting the crotch size of said diaper.

2. The reusable, washable cloth diaper set forth in claim 1, wherein said rear wings further include means for securing said diaper in a rolled up storage and transport position.

3. The reusable, washable cloth diaper set forth in claim 1, wherein means for adjusting the waist size of said diaper includes two parallel, horizontal rows of snaps disposed across a front portion of said diaper and correspond with snaps attached to said rear wings.

4. The reusable, washable cloth diaper set forth in claim 1, wherein means for adjusting the crotch size of said diaper include two vertical rows of snaps on a front portion of said diaper, wherein a top pair of said snaps may be attached to snaps positioned therebelow.

5. The reusable, washable cloth diaper set forth in claim 1, further including elastic means positioned between said inner layer and said outer layer along edges of a narrow section of said diaper, so that said elastic means may move freely between said inner layer and said outer layer.

6. The reusable, washable cloth diaper set forth in claim 1, wherein said inner layer and said flaps are made from bamboo jersey fleece.

* * * * *